United States Patent
Situ et al.

(10) Patent No.: US 9,297,797 B2
(45) Date of Patent: Mar. 29, 2016

(54) ION SELECTIVE ELECTRODE MODULE FOR CLINICAL DIAGNOSTICS

(75) Inventors: Richard Lou Situ, Placentia, CA (US); Youqin E. Xie, Diamond Bar, CA (US); Yuan M. Xie, legal representative, Diamond Bar, CA (US)

(73) Assignee: Beckman Coulter, Inc., Brea, CA (US)

( * ) Notice: Subject to any disclaimer, the term of this patent is extended or adjusted under 35 U.S.C. 154(b) by 583 days.

(21) Appl. No.: 12/827,975

(22) Filed: Jun. 30, 2010

(65) Prior Publication Data
US 2011/0000796 A1     Jan. 6, 2011

Related U.S. Application Data

(60) Provisional application No. 61/222,360, filed on Jul. 1, 2009.

(51) Int. Cl.
*G01N 33/49* (2006.01)
*G01N 27/333* (2006.01)

(52) U.S. Cl.
CPC .......... *G01N 33/4915* (2013.01); *G01N 27/333* (2013.01)

(58) Field of Classification Search
CPC ............. G01N 27/333; G01N 33/4915; B01L 2300/0861; B01L 2300/0816; B01L 3/5027
USPC ........ 204/267, 232; 205/779, 789.5, 792, 789
See application file for complete search history.

(56) References Cited

U.S. PATENT DOCUMENTS

| | | | |
|---|---|---|---|
| 4,003,705 A | | 1/1977 | Buzza et al. |
| 4,169,125 A | * | 9/1979 | Rodriguez et al. ............... 422/65 |
| 4,490,235 A | * | 12/1984 | Calzi .............................. 204/409 |
| 4,531,088 A | | 7/1985 | Czaban et al. |
| 4,535,786 A | * | 8/1985 | Kater ............................. 600/573 |
| 4,596,649 A | | 6/1986 | Hofmeier et al. |
| 4,640,821 A | * | 2/1987 | Mody et al. ....................... 422/81 |
| 4,797,191 A | | 1/1989 | Metzner et al. |
| 4,888,998 A | | 12/1989 | Buzza et al. |
| 4,889,611 A | | 12/1989 | Blough |
| 4,920,056 A | * | 4/1990 | Dasgupta ......................... 436/50 |
| 4,965,049 A | | 10/1990 | Lillig et al. |

(Continued)

FOREIGN PATENT DOCUMENTS

| | | |
|---|---|---|
| EP | 0 101 236 A2 | 2/1984 |
| WO | WO 88/08973 A1 | 11/1988 |
| WO | WO 2007/008245 A2 | 1/2007 |

OTHER PUBLICATIONS

PCT International Search Report mailed Sep. 29, 2010; International Application No. PCT/US2010/040637, 3 pgs.

*Primary Examiner* — Luan Van
*Assistant Examiner* — Louis Rufo
(74) *Attorney, Agent, or Firm* — Merchant & Gould P.C.

(57) ABSTRACT

A method of determining an electrolyte in a sample including adding the sample to an electrolyte module, the electrolyte module including a dilution cup, a flow cell, and a pump, the flow cell having a flow channel with a first end and a second end, the first end fluidically coupled to the dilution cup, and the second end fluidically coupled to the pump; combining the sample with a diluent in the dilution cup to produce a diluted sample; operating the pump to aspirate the diluted sample into the flow cell; measuring the electrolyte in the diluted sample in the flow cell; and reversing the pump to dispense fluid through the second end to displace the diluted sample from the flow cell back into the dilution cup.

16 Claims, 8 Drawing Sheets

(56) References Cited

U.S. PATENT DOCUMENTS

| | | |
|---|---|---|
| 5,130,095 A | 7/1992 | Ricchio et al. |
| 5,213,762 A | 5/1993 | Ricchio et al. |
| 5,223,222 A | 6/1993 | Ricchio et al. |
| 5,294,311 A | 3/1994 | McNeal et al. |
| 5,833,925 A | 11/1998 | Shu et al. |
| 6,475,441 B1 * | 11/2002 | Parce et al. .................. 436/179 |
| 6,719,888 B1 | 4/2004 | Chan et al. |
| 2004/0188252 A1 | 9/2004 | Chan et al. |
| 2005/0095724 A1 * | 5/2005 | Shibutani et al. ............. 436/180 |
| 2007/0202608 A1 * | 8/2007 | Uffenheimer et al. ......... 436/180 |

* cited by examiner

ION SELECTIVE ELECTRODE MODULE FOR CLINICAL DIAGNOSTICS

CROSS-REFERENCE TO RELATED APPLICATIONS

This application claims the benefit of U.S. Provisional Application No. 61/222,360 filed Jul. 1, 2009, and is entirely incorporated by reference herein.

TECHNICAL FIELD

The present invention relates generally to assays involving an ion selective electrode (ISE).

BACKGROUND

Analyzing clinical samples such as serum and urine with ISE devices involves multiple readings of a test solution using a plurality of ion specific analyte electrodes. Generally, an analyte electrode responds to a particular ion activity. In some ISE systems, generally termed indirect ISE systems, the test solution is mixed with a diluent producing an assay mixture. Use of diluted test solutions reduces the amount of test solution required and reduces the detrimental effect of materials such as protein that may be present at high concentration in some test solutions. In some systems, different aliquots of the same test solution or assay mixture may be applied to individual devices having different specific electrodes. Other systems combine several electrodes in one measuring device determining multiple ion activities from a single aliquot of test solution. Existing multi-electrode ISE devices, however, may use bulky configurations to provide the appropriate fluid flow over a plurality of electrodes and may require relatively large amounts of test solution to perform accurate mixing and measurements.

Generally, an ion selective electrode (ISE) is a sensor that responds to the activity of a specific ion in a solution by electrical means. The sensor, in cooperation with other components, translates the activity of a specific ion into a measurable electrical potential. The sensing portion of the electrode is usually made of an ion-specific membrane. A reference electrode completes an electric circuit for measuring the electrical potential. Commonly, a grounding connection ties the solution to system electrical ground to minimize electrical noise and to bring the potential into a range compatible with measurement electronics. The voltage developed between the analyte electrode and the reference electrode may be used to determine the activity of ions in the solution.

Ion-selective electrodes are widely used in biochemical and biophysical assays for measurements of ionic concentration in aqueous solutions. Clinical electrolyte assays frequently employ ISEs to determine multiple ion activities in serum, plasma, cerebrospinal fluid, or urine. Such test solutions are usually available in very limited quantities. Existing ISE systems use as small a volume of such test solutions as practical, but the volume used is still quite large; some systems use 65 microliters or more. This is ten to twenty times the volume used for other routine clinical assays.

Generally, a clinical ISE system constantly interchanges the fluids that fill it, presenting to the electrodes in turn a first assay mixture, a reference solution, a second assay mixture, a reference solution, etc. Any amount of a previous fluid that remains within the system must be a small enough proportion of the volume of the next fluid that it contributes no more than a negligible effect on the measured result. Thus the volume of an ISE system has a two-fold influence on the amount of test solution required; first, enough assay mixture must be available to fill the volume; second, the volume of assay mixture must be much greater than any residual volume of a prior fluid. The amount of residual fluid depends upon the area of wetted surface and upon the geometry of that surface. Tight corners, complex shapes exposed to wetting, unswept dead volumes, and rough surfaces all increase the amount of residual fluid and require more assay mixture, and hence more of the scarce test solution.

One test solution reduction strategy commonly employed is to expose a single aliquot of test solution to multiple electrodes. Several drawbacks may exist in existing multi-electrode ISE testing devices. For example, some existing systems may use separate, disjoint components to form the multi-electrode ISE assay system. Generally, fluid connectors and tubing connect disjoint elements of existing ISE systems to interconnect a working system. These disjoint systems may require large amounts of test solution to fill the fluid connectors and tubing between the disjoint elements. Still more test solution may be required to rinse prior fluids from the tubing and from dead spaces in fluid connectors.

Moreover, some existing systems are inefficient in preparing a sample for testing. In particular, mixing precision and efficiency may be problematic in some indirect ISE systems. Some ISE systems may use a mechanical stir bar to mix a test solution with a diluent. Stir bars and similar mixers with their associated drive mechanisms add mechanical and operational costs to an ISE system. Stir bars also need thorough cleaning between applications of different test solutions to prevent cross-contamination (i.e. carryover) that may skew test results. Further, the stir bar requires a minimum amount of fluid to mix effectively, thereby placing additional volume constraints on scarce test samples.

Other clinical ISE systems use a closed injection port where a stream of diluent interacts with a stream of test solution delivered by a probe sealed into the injection port. Fluid mixing in such systems is dependent on the interpenetration of liquid streams from two sources, a process directly opposed by fluid viscosity. Relatively high fluid injection velocities are required to produce this mixing. Maintaining the desired ratio of test solution to diluent under such conditions generally requires a pump that is inherently ratiometric, such as a multi-chamber positive displacement ratio pump. Such pumps have proven problematic, in part due to leakage at multiple seals that produce undesired fluid junctions that upset electrode potentials. All surfaces of the closed injection port need thorough cleaning between applications of different test solutions to prevent carryover that may skew test results. Further, the probe seal in such systems is a wear part that may require frequent maintenance.

Another problem with some existing systems may involve the grounding configuration of these systems. As described above, typical ISE systems use a ground connection to bring the assay mixture potential into measurable range for the electronics. Existing ISE systems may use a solution ground that is a conductive tube suspended and immersed in the assay mixture or a grounding plate disposed in flow channels between the analyte electrodes. The ground may be anchored by a coupling that requires glue. The glue may contaminate the assay mixture, causing unwanted electrical noise, drift, or skewing in the measurements of the ISE system. Grounding plates suspended in flow channels may create dead volumes and crevices that are difficult to clean, increasing the volume of test solutions needed. Further, the solution ground may be difficult to insert, assemble, or connect, adding to the expense of construction of an ISE system.

Yet another issue with some existing systems is the requirement of a ratio pump or other multi-chamber pump to precisely control the movement of test solution, diluent, reference buffer, and other solutions through the flow cell from a dilution cup. Due to the pump design, the solutions are able to wick from one chamber to another, thereby contaminating the solutions in the chambers. Because not all solutions are used at the same time, the solutions are repeatedly cycled (e.g. diluent is aspirated and dispensed back to its source) and therefore more likely to contaminate the entire system. The wicking between chambers may also produce a half-cell; the resulting potential may skew the ISE measurements. Ratio pumps and other multi-chamber pumps may be expensive and difficult to maintain. Because of the number of components of these pumps and complexity of operation, mechanical failures may occur frequently. These failures may also be difficult and time consuming to repair.

SUMMARY

The indirect ISE method and system described determines a plurality of ion activities in a single aliquot of test solution using an integrated body including an open dilution cup, a solution ground that takes the form of an analyte electrode, a simple and efficacious mixing scheme, and a simplified two-way flow process. The integrated body reduces the space required for the system and reduces the volume of test solution required. The ground electrode reduces the volume of test solution required by reducing carryover, and provides placement flexibility to minimize electrical noise. The open dilution cup uses a sequence of diluent injections to precisely dilute and thoroughly mix a test solution without the use of additional mixing hardware such as stir bars, improving performance and further reducing the volume of sample required. The two-way flow process reduces the system complexity, reduces carryover, and improves performance by eliminating extraneous potentials associated with problematic multistage ratio pumps.

The ISE method for determining an electrolyte in a sample may include adding the sample to an electrolyte module, the electrolyte module including a dilution cup, a flow cell, and a pump, the flow cell having a flow channel with a first end and a second end, the first end fluidically coupled to the dilution cup, and the second end fluidically coupled to the pump; combining the sample with a diluent in the dilution cup to produce a diluted sample; operating the pump to aspirate the diluted sample into the flow cell; measuring the electrolyte in the diluted sample in the flow cell; and reversing the pump to dispense fluid through the second end to displace the diluted sample from the flow cell back into the dilution cup.

DETAILED DESCRIPTION

Figure 1:
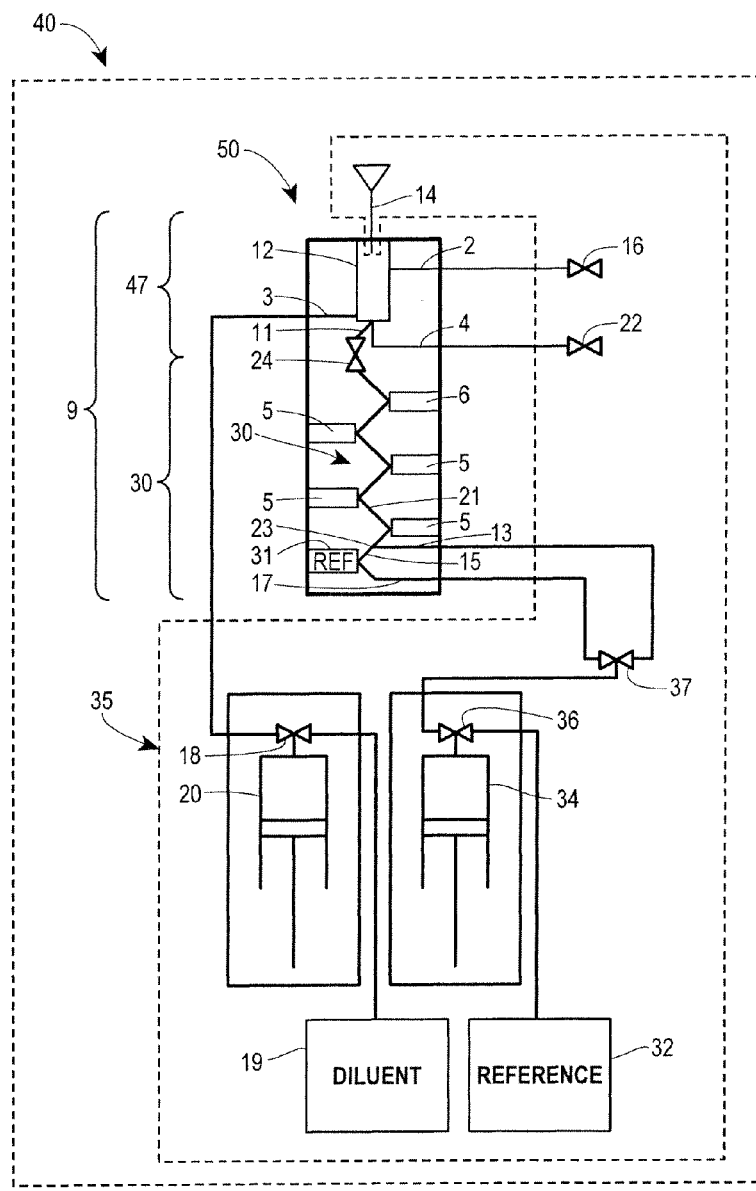
FIG. 1 illustrates a function diagram for an embodiment of an improved multi-electrode ISE system including an integrated assembly.

Turning now in detail to the drawings, FIG. 1 illustrates a schematic diagram of one embodiment of an improved ISE system 40, which indirectly determines ion activities of test solutions by measuring electrode potentials. ISE system 40 includes integrated assembly 50 and supporting fluidics 35.

Structurally, integrated assembly 50 is a substantially solid body incorporating a collection of cavities, channels, and components defining upper path 47 and flow cell 30. Upper path 47 includes dilution cup 12, wash conduit 2, diluent conduit 3, drain conduit 4, transfer conduit 11, and isolation valve 24. Flow cell 30 includes main channel 21, analyte electrodes 5, ground electrode 6, reference electrode 31 (any two or more of the last three collectively "electrodes"), exit conduit 13, side channel 15, and reference conduit 17.

Central to upper path 47 is dilution cup 12. Dilution cup 12 is an elongated cavity formed within integrated assembly 50 and terminating at opening 1 at the top of integrated assembly 50. Dilution cup 12 connects to four fluid conduits formed within integrated assembly 50. Wash conduit 2, diluent conduit 3, and drain conduit 4 each extend from dilution cup 12 to the outside of integrated assembly 50 where each couples to supporting fluidics 35. Transfer conduit 11 extends from dilution cup 12 to the inlet of isolation valve 24. Diluent conduit 3, drain conduit 4, and transfer conduit 11 connect to dilution cup 12 near the bottom of dilution cup 12. Wash conduit 2 connects to dilution cup 12 nearer the top of dilution cup 12.

Flow cell 30 extends from the outlet of isolation valve 24 as main channel 21. Main channel 21 connects to one or more analyte electrodes 5 and to ground electrode 6. Main channel 21 continues beyond its connections to analyte electrodes 5 and ground electrode 6 to intersection 23. At intersection 23, main channel 21 branches into side channel 15 and exit conduit 13. Exit conduit 13 extends from intersection 23 to the outside of integrated assembly 50 where it couples to supporting fluidics 35. Side channel 15 extends from intersection 23 to couple with reference conduit 17 at reference electrode 31.

Supporting fluidics 35 include probe 14, diluent valve 18, diluent container 19, diluent pump 20, drain valve 22, reference pump 34, reference container 32, bi-directional valve 37, reference valve 36, and wash valve 16.

Probe 14 is a conventional fluid transfer probe capable of moving vertically and disposed to enter dilution cup 12 through opening 1. Probe 14 couples to a pump (not shown) allowing probe 14 to transfer fluids to dilution cup 12.

Diluent pump 20 couples fluidically to the common connection of diluent valve 18. Diluent valve 18 is a three-way valve; the remaining connections of diluent valve 18 couple to diluent reservoir 19 and to diluent conduit 3. The net effect of these connections is that diluent pump 20 fluidically couples to either diluent container 19 or to diluent conduit 3, depending on the state of diluent valve 18.

In a similar manner, reference pump 34 couples fluidically to the common connection of reference valve 36. Reference valve 36 is a three-way valve; the remaining connections of reference valve 36 couple to reference container 32 and to the common connection of bi-directional valve 37. The net effect of these connections is that reference pump 34 fluidically couples to either reference container 32 or to bi-directional valve 37, depending on the state of reference valve 36. Bi-directional valve 37 is also a three-way valve; the remaining connections of bi-directional valve 37 couple to reference conduit 17 and to exit conduit 13. The net effect of the combination of connections involving reference valve 36 and bi-directional valve 37 is that reference pump 34 fluidically couples to one of reference container 32, reference conduit 17, and exit conduit 13 depending upon the state of reference valve 36 and bi-directional valve 37.

Drain valve 22 is an on-off type valve. One side of drain valve 22 fluidically couples to drain conduit 4. The second side of side of drain valve 22 connects to a source of vacuum or suction. Wash valve 16 is also an on-off type valve. One side of wash valve 16 fluidically couples to wash conduit 2. The second side of side of wash valve 16 connects to a source of wash fluid under pressure.

Integrated assembly 50 and supporting fluidics 35 cooperate to manipulate and measure a number of working fluids. Working fluids include test solutions, diluent, assay mixtures, reference solution, wash fluid, and wastes.

Test solution is the material or sample assayed for ion activity. Test solution is usually a body fluid such as blood, plasma, serum, urine, or cerebrospinal fluid with unknown ion activity. Some test solutions, particularly cerebrospinal fluid and blood fractions from pediatric and geriatric patients, are available in very limited amounts. Conserving such precious test solutions is an important requirement of ISE system 40. Calibrators and controls of predetermined ion activity may also be test solutions. The purpose of calibrators is to correlate raw electrode potential measurements to ion activity. The purpose of controls is to verify the proper operation of ISE system 40; when operating properly, ion activity determinations of controls must fall within acceptable limits.

Diluent is a buffer of controlled pH and ionic composition mixed in predetermined proportion with test solutions to form assay mixtures. Dilution of test solution with diluent performs two valuable functions. First, it lowers the concentration of potentially interfering substances such as protein. Protein can accumulate over time on electrode surfaces, limiting electrode response time and shortening lifetime. Diluting the test solution reduces exposure of electrodes to high protein concentrations and delays or limits the deleterious effects. The typical log-linear relationship between electrode potentials and ion activities assures that the same span of electrode potentials remain available for diluted assay mixtures as for neat test solutions. Second, dilution of test solution reduces the volume of test solution needed for ion activity measurement. Upper path 47 and flow cell 30 of ISE system 40 must be filled with the fluid to be assayed for ion activity. Less test solution is required if only a fraction of that fluid is test solution. Further, upper path 47 and flow cell 30 must be adequately rinsed with each fluid so as to displace any remnants of prior fluids that might further dilute the assay mixture and alter the apparent ion activity. Less test solution is required if only a fraction of that fluid is test solution. The dilution ratio between test solution and diluent in assay mixtures is typically in the range of about 1:1 to about 1:100, preferably about 1:10 to about 1:30, and most preferably about 1:20. The dilution ratio between test solution and diluent may be altered for different test solution such as serum and urine.

Assay mixture is the result of combination and mixing of test solution and diluent in a predetermined dilution ratio.

Reference solution is another buffer of controlled pH and ionic composition. Reference buffer serves several purposes. First, it provides a stable ionic environment for reference electrode 31. Second, it intermittently provides a known ionic environment to electrodes 5 and 6 to indicate or counteract drift of electrode potentials. Third, reference solution rinses at least parts of flow path 9 to remove any vestiges of used assay mixture that might dilute the reference solution or interfere with subsequent measurements.

Wash solution is a liquid used to rinse components of ISE system 40. Wash solution may be largely deionized water and may contain surfactants to aid in rinsing of components wetted by other working fluids in the course of determinations.

The various working fluids become wastes once used by ISE system 40. Wastes are typically removed to make further determinations.

Functionally, integrated assembly 50 cooperates with supporting fluidics 35 by manipulating working fluids through flow path 9. Flow path 9 includes upper path 47 and flow cell 30. Upper path 47 has a first purpose to prepare the assay mixture for ion activity measurement and a second purpose to drain the contents of flow path 9 and prepare for the next measurement. In some embodiments, upper path 47 may have the third purpose of cleaning probe 14. The assay mixture prepared within upper path 47 transfers to flow cell 30 for electrode response measurement. Flow cell 30 has the additional purposes of measuring electrode response to reference solution and of returning waste to upper path 47 for drainage.

Upper path 47 cooperates with supporting fluidics 35 to prepare the assay mixture. This cooperation includes the functions of test solution addition, diluent addition, mixing of test solution and diluent to produce assay mixture, and transfer of the prepared assay mixture to flow cell 30.

Probe 14, a conventional fluid transfer probe, delivers test solution directly to dilution cup 12 by descending through opening 1 and injecting test solution in concert with delivery of diluent as described more fully below.

Diluent pump 20 delivers diluent stored in diluent container 19 through diluent conduit 3 in cooperation with diluent valve 18. Diluent pump 20 delivers a precise amount of diluent to assure a repeatable dilution ratio in the assay mixture and is preferably a positive displacement pump such as a piston pump or syringe pump. Diluent valve 18 is a three-way valve such as a solenoid valve or a shear valve. Diluent valve 18 alternately couples diluent pump 20 to diluent container 19 to fill diluent pump 20 and to diluent conduit 3 to transfer the metered diluent to dilution cup 12.

Transfer conduit 11 connects dilution cup 12 to isolation valve 24. The purpose of transfer conduit 11 is to transfer assay mixture prepared in dilution cup 12 through isolation valve 24 to flow cell 30, where assay mixture ion activity may be measured. Isolation valve 24 prevents transfer until the test solution mixes thoroughly with diluent, and thereby assures that measurement of ion activity takes place on a uniformly mixed, representative aliquot of the assay mixture. Isolation valve 24 is preferably a zero-dead volume valve to prevent cross-contamination of assay mixtures; it blocks transfer when closed and permits transfer when open. Preferably, transfer conduit 11 connects near the bottom of dilution cup 12 to conserve assay mixture and to avoid transferring air to isolation valve 24.

Drain conduit 4 and wash conduit 2 cooperate with parts of supporting fluidics 35 to support the secondary purpose of upper path 47 by draining and cleaning dilution cup 12. Waste exits dilution cup 12 through drain conduit 4 under control of drain valve 22. Drain valve 22 preferably connects to a vacuum source to drain dilution cup 12 when drain valve 22 is open. Drain conduit 4 preferably connects at or near the bottom of dilution cup 12, taking advantage of gravity-assisted flow to more completely drain dilution cup 12.

Wash fluid enters dilution cup 12 through wash conduit 2 under control of wash valve 16 to rinse the walls of dilution cup 12. Preferably, wash conduit 2 connects to dilution cup 12 above the connections of diluent conduit 3, drain conduit 4, and transfer conduit 11. This helps assure thorough rinsing by dissolving or displacing any dried salts or contaminants downward in dilution cup 12 toward drain conduit 4.

In some embodiments, dilution cup 12 may also clean probe 14. Probe 14 may exhaust any residual test solution chased by wash fluid into dilution cup 12. These dirty fluids may then exit via drain conduit 4. Clean wash fluid may then substantially fill dilution cup 12 either through probe 14 or through wash conduit 2. Probe 14 may then descend into dilution cup 12 where the clean wash fluid may rinse the outside of probe 14. Probe 14 may then ascend and the now used wash fluid may exit through drain conduit 4. An additional rinse and drain of dilution cup 12 with fresh wash fluid may complete the process.

Flow cell 30 measures the ion activity of fluids filling it. These measurements form the basis for ion activity determinations. Flow cell 30 measures ion activity by exposing fluids to electrodes which develop electrical potential in response to that exposure. This process requires cooperation between flow cell 30 and supporting fluidics 35.

Main channel 21 within flow cell 30 connects the outlet of isolation valve 24 to the responsive portions of each analyte electrode 5 and ground electrode 6. Side channel 15 further connects main channel 21 to the responsive portion of reference electrode 31 and to reference conduit 17. Main channel 21 need not be straight; it may change directions along its course for mechanical convenience in manufacture and to allow compact packing of relatively large electrodes 5 and 6. Preferably, main channel 21 is unbranched so that each element of fluid passing from isolation valve 24 to exit conduit 13 contacts ground electrode 6 and each analyte electrode 5. This unbranched structure reduces unswept volumes that might otherwise cross-contaminate successive assay mixtures.

Ground electrode 6, one or more analyte electrodes 5, and reference electrode 31 contact fluids in flow cell 30. External measurement electronics (not shown) electrically couple to each of electrodes 5, 6, and 31. Filling main channel 21 and side channel 15 with conductive fluid, such as assay mixture or reference solution, establishes an electrical connection between electrodes 5, 6, and 31. This electrical connection permits external measuring electronics to complete an electrical circuit and measure the electrode potentials developed between analyte electrodes 5 and reference electrode 31.

Each analyte electrode 5 is an electrical half cell contributing to an electrode potential in response to target ion activity in the assay mixture. Analyte electrodes 5 may target several different ions. For example, commonly assayed ions in body fluids include ions of sodium, potassium, lithium, magnesium, calcium, carbonate, and chloride, among others. Accordingly, each analyte electrode 5 may target any of these ions either singly or in combination. Preferably, ISE system 40 incorporates analyte electrodes 5 targeted to sodium, potassium, calcium, and chloride ions. Each analyte electrode 5 has a responsive portion which, when exposed to assay mixture or reference solution, causes the analyte electrode 5 to respond electrically to the ion activity. The responsive portions of each analyte electrode 5 comprise any of a number of ion responsive materials known in the art including silver-silver chloride pellets, glass membranes, and polymeric membranes, among others. Preferably, analyte electrodes 5 targeted to metal cations such as sodium, potassium, and calcium, include glass or polymeric membranes. Analyte electrodes 5 targeted to chloride may include polymeric membranes, hydrophobic ion exchangers, or preferably, a silver-silver chloride pellet.

The responsive portions of analyte electrodes 5 may take a number of physical forms including hollow tubes or planar regions. Preferably, the responsive portions are disk-shaped regions located at one end of generally rod-shaped analyte electrodes 5. Alternatively, analyte electrodes 5 with tubular responsive portions may form at least a portion of main channel 21 by abutting the tubular portions one to another.

An electrical half cell is essentially one terminal of a battery; any electrode potential measured must be referred to another terminal that serves to complete the electrical circuit. Reference electrode 31 acts as a second terminal to support current flow producing measurable electrode potentials between reference electrode 31 and each analyte electrode 5. Reference electrode 31 itself responds to ion activity. To provide a stable contribution to electrode potentials, its responsive region must remain in contact with a fluid of fixed ion activity, such as reference solution, during measurement.

Ground electrode 6 electrically connects to system electrical ground and, when in contact with assay mixture in main channel 21, grounds the otherwise floating contents of flow cell 30. This has two purposes. First, it assures compatibility of electrode potentials with measurement electronics, which normally have limited dynamic range centered at or near system ground. Were the contents of flow cell 30 left floating, the electrode potentials might drift outside of the dynamic range of the measurement electronics. Grounding prevents this. Second, tying the contents of flow cell 30 to system ground helps reject electrical noise from the electrode potentials.

Although ground electrode 6 may take a broad variety of physical forms, such as a wire or grounding plate suspended in flow cell 30 or grounded conductive conduits glued into integrated assembly 50, substantial advantages result from use of ground electrodes in similar form to analyte electrodes 5. This permits production of ground electrode 6 to share in at least some of the economies of scale associated with the larger production volumes of analyte electrodes 5. Further, the common physical form permits a common method of mounting ground electrode 6 and analyte electrodes 5 within integrated assembly 50. This saves the expense and complexity of developing different mounting methods. The common physical form also aids design flexibility as ground electrode 6 may be interchanged in position with any of analyte electrodes 5 within integrated assembly 50 to optimally reject electrical noise.

As mentioned above, the responsive region of reference electrode 31 preferably remains in reference solution during measurement. Reference solution reaches reference electrode 31 through reference conduit 17. Reference pump 34 delivers reference solution stored in reference container 32 in cooperation with reference valve 36 and bi-directional valve 37. Reference pump 34 is preferably a positive displacement pump such as a piston pump or syringe pump capable of aspirating and delivering precise amounts of reference solution. Reference valve 36 is a three-way valve such as a solenoid valve or a shear valve that alternately couples reference pump 34 to reference container 32 to aspirate and to bi-directional valve 37 to aspirate or to deliver. Bi-directional valve 37 is a three-way valve such as a solenoid valve or a shear valve. Bi-directional valve 37 couples reference valve 36 either in a first position to exit conduit 13 or in a second position to reference conduit 17. In the first position, fluid flows to main channel 21 through exit conduit 13. In the second position reference fluid flows through reference conduit 17 to reference electrode 31 and to side channel 15.

Reference pump 34 is capable of either aspirating or delivering fluid through bi-directional valve 37. By setting bi-directional valve 37 in the second position, reference pump 34 may dispense sufficient reference fluid to fill reference conduit 17 and side channel 15, immersing the responsive portion of reference electrode 31 in reference solution. By setting bi-directional valve 37 in the first position and opening isolation valve 24, reference pump 34 may aspirate contents of dilution cup 12 into main channel 21 and exit conduit 13. The flow down main channel 21 "shears off" the reference solution in side channel 15 leaving it in contact with assay mixture from dilution cup 12. The juxtaposition of the two different fluids at intersection 23 of side channel 15 and main channel 21 forms a liquid junction. This liquid junction electrically couples reference electrode 31 (continuously exposed to reference fluid) and analyte electrodes 5 (exposed to assay mixture transferred from dilution cup 12).

Figure 2A:
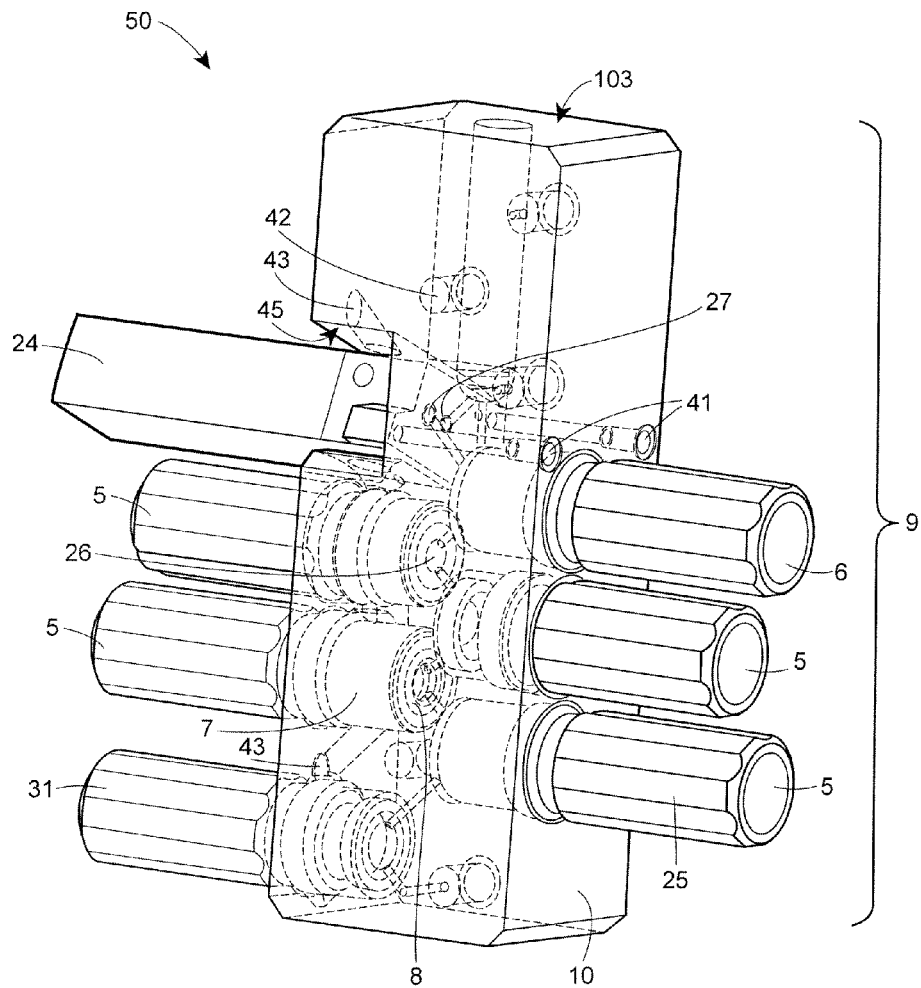
FIG. 2A illustrates an embodiment of the integrated assembly that integrates various components into an integrated body.

FIG. 2A illustrates in greater detail an embodiment of integrated assembly 50. In this embodiment, integrated assembly 50 comprises substantially solid integrated body 10 formed to include a collection of cavities, channels, conduits, and ports where the conduits intersect the block surfaces. Mounted to integrated body 10 are isolation valve 24, analyte electrodes 5, ground electrode 6, and reference electrode 31.

Integrated body 10 may be formed of any nonporous, nonconductive material. Preferably, integrated body 10 is transparent with polished surfaces to easily visualize and locate any flow obstructions, bubbles, or leaks. Suitable materials include: easily-formed polymers such as PVC, silicone rubber, acrylic, polycarbonate, and polystyrene; glasses and ceramics; and metals with nonconductive coatings. Preferably, integrated body 10 is formed of transparent acrylic plastic. Integrated body 10 may be formed in any of a number of shapes such as an elongated body with circular or "D-shaped" cross section. Preferably integrated body 10 is generally rectangular with substantially parallel opposing sides for ease of manufacture and mounting. Integrated body 10 has its vertical orientation defined by top surface 103.

Integrated body 10 may be formed by any of a variety of production processes including casting, injection molding, stereolithography, 3-D printing, bonding of separately formed layers, or machining but is preferably machined. Machining acrylic can produce smooth channels that reduce fluid carryover and retard protein build up, thereby improving system performance.

Isolation valve 24 is a solenoid controlled on-off valve coupled to integrated body 10 and in fluid communication with integrated body 10. The internal fluid pathway of isolation valve 24 forms part of fluid path 9 as disclosed above. Isolation valve 24 is preferably a zero-dead volume valve without unswept crevices or cavities that might trap fluid and contaminate subsequent assay mixtures. Isolation valve 24 may be attached to integrated body 10 through any of a variety of techniques including press fit with compliant seals, threaded valve bodies, and adhesives. Preferably, isolation valve 24 fits within valve slot 45 formed into integrated body 10 and is attached to integrated body 10 using machine screws passing through counter-bored holes 41. Compliant seals 27 compressed by tightening the screws prevent leaks in fluid connections between isolation valve 24 and integrated body 10.

Integrated assembly 50 incorporates a single ground electrode 6, a single reference electrode 31, and multiple analyte electrodes 5. Electrodes 5, 6, and 31 are the source of the electrical signals that permit determination of ion activity. As disclosed above, each electrode has a responsive portion. The responsive portions of each analyte electrode 5 and reference electrode 31 incorporate ion responsive materials, such as ISE membranes known in the art. The responsive portion of ground electrode 6 is a conductor, such as a stainless steel or carbon rod, electrically connected to system electrical ground. Preferably, each electrode has similar shape to permit a common mounting geometry and to take advantages of economies of scale in manufacturing. Use of a common mounting geometry allows flexibility of placement of at least some electrodes at different locations in integrated body 10. The common geometry also simplifies assembly and maintenance by limiting the number of different procedures required.

Although electrodes may take any of a variety of shapes, preferably, and as shown in the embodiment of FIG. 2A, each electrode is roughly cylindrical. Also preferably, active region 26 disposed axially on the disk-shaped end surface of the cylinder forms the responsive region. Each roughly cylindrical electrode includes electrode body 7 with active region 26, electrode nut 25, face seal 8, and cable (not shown). Electrode body 7 is substantially cylindrical and fits within electrode nut 25. Face seal 8 is disposed axially on the disk-shaped end surface of electrode body 7 and surrounds at least a portion of active region 26.

Analyte electrodes 5 have a limited useful life generally determined by leaching of labile components from electrode membranes and may be replaced from time to time. The mounting of electrodes to integrated body 10 is designed to facilitate this replacement process. Although electrodes may mount to integrated body 10 in a variety of methods such as bayonet mount, snap fit, or compression fit, electrode nut 25 is preferably threaded and mates with complementary threads in integrated body 10. Electrode body 7 fits within electrode nut 25 such that, when the threads of electrode nut 25 engage the complementary threads of integrated body 10, electrode body 7 is advanced into integrated body 10 until face seal 8 contacts the surface of integrated body 10 and forms a fluid tight seal around active region 26. Knurling or other gripping features on the external aspect of electrode nut 25 facilitate installation and removal.

Integrated body 10 may incorporate ancillary features for mechanical convenience. Runout holes 43 allow machine tool or molding core pin access for convenient forming of fluid channels within integrated body 10. Mounting holes 42 (best visible in FIG. 4) serve to attach integrated body 10 to external mounting hardware (not shown).

Figure 2B:
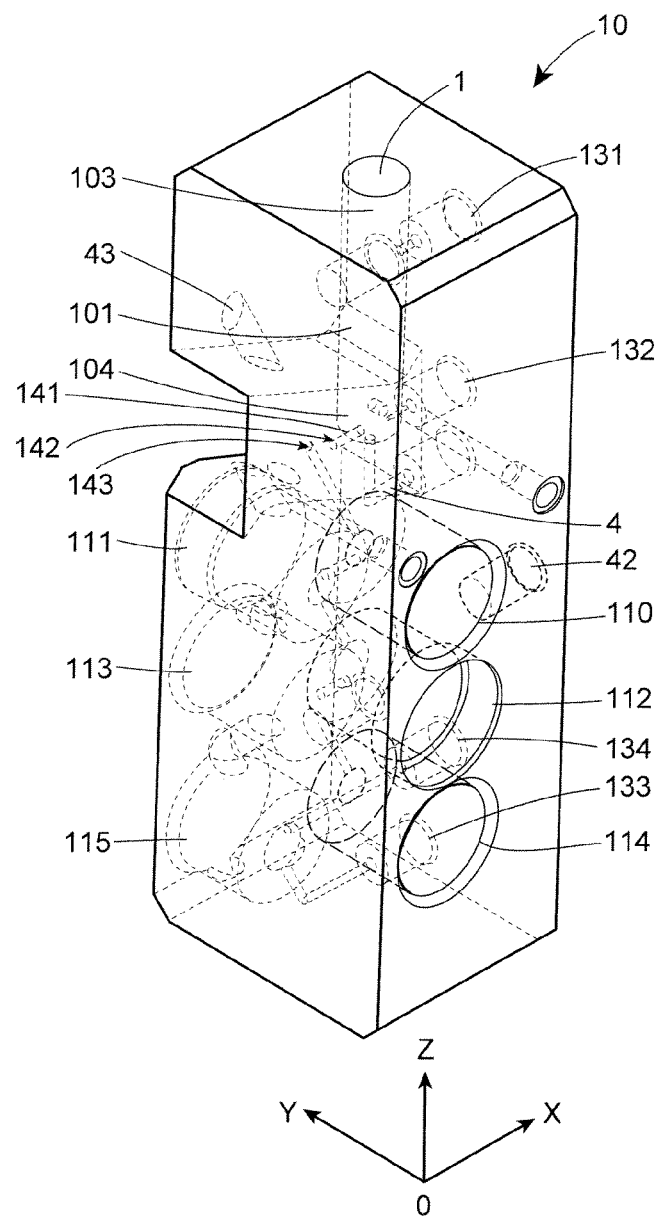
FIG. 2B illustrates the integrated body of FIG. 2A.

FIG. 2B illustrates the same embodiment of integrated body 10 as FIG. 2A but with the mounted components removed to better visualize internal structure. FIGS. 3-6 illustrate orthogonal views of the same embodiment of integrated body 10 as FIG. 2B and will occasionally be referred to for clarity. The cavities, channels, conduits, and ports of integrated body 10 define flow path 9 allowing entry and egress of fluids from integrated body 10 and interconnecting isolation valve 24 with electrodes 5, 6, and 31.

Cavities, channels, conduits, and ports within integrated body 10 may be of any shape and size to reasonably fulfill their purpose of transporting fluids. Among reasonable cross-sectional shapes are circular, semi-circular, and rectangular. A circular cross section is preferable to reduce fluid retention at corners with small internal radii. A trade off among several factors determines the diameter of conduits and channels such as drain conduit 4. Large diameters produce low flow resistance but require large fill volumes; small diameters undesirably increase flow resistance and may be plugged or occluded by debris or bubbles. Preferably, the diameter of conduits and channels within integrated body 10 is in the range of 0.010 to 0.100 inches and most preferably about 0.040 inches. This size is large enough to reduce flow resistance to a manageable level and to clear debris normally encountered in clinical samples.

Ports, such as wash port 131, are disposed where fluid conduits intersect the exterior surfaces of integrated body 10. The purpose of ports is to connect the fluid conduits to supporting fluidics 35 so that fluids may be transferred into and out of flow path 9 without leaks or unswept dead zones. Each port generally includes a counter-bore to mate with supporting fluidics 35 of FIG. 1. The counter-bore of a port may connect to supporting fluidics 35 through a fluidic connector such as a glued or press-fit tube (not shown). Alternatively, a commercial fluidic connector may be used, such as the Upchurch P-201 Flangeless Nut fitting manufactured by IDEX® Corporation of Northbrook, Ill. When a commercial fluidic connector is used, the port requires mating features, such as threads, tapers, or defined counter-bore dimensions appropriate to the commercial fluidic connector. Preferably, each port accommodates a commercial fluidic connector to connect to supporting fluidics 35.

Figure 3:
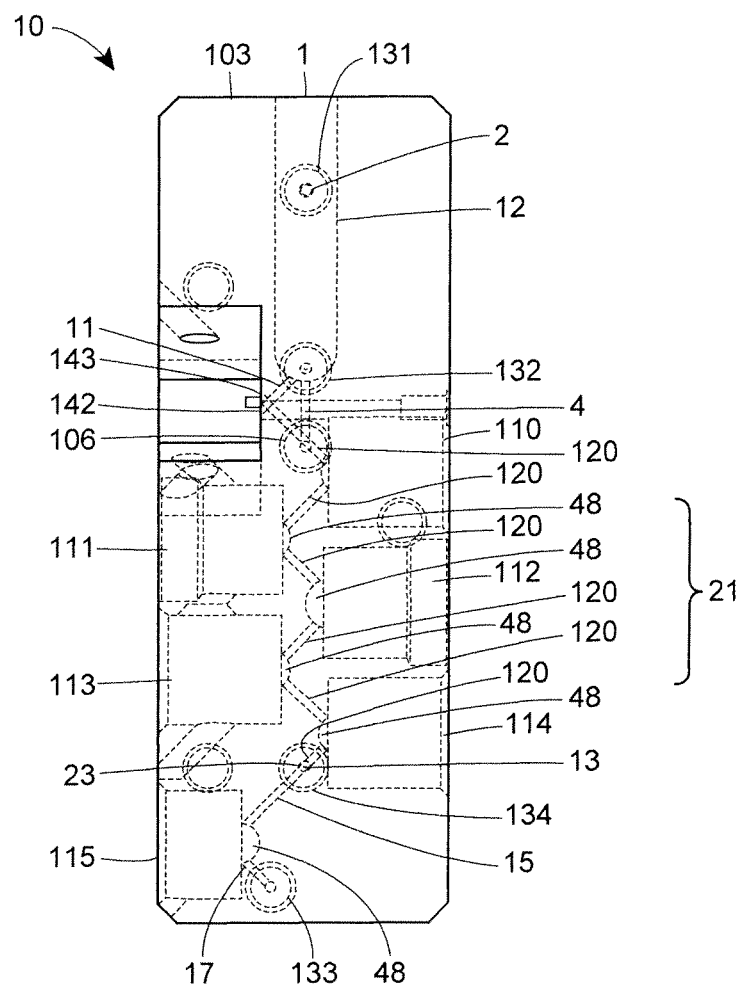
FIG. 3 illustrates a view of the integrated body of FIG. 2B along a line O-X of FIG. 2B.
Figures 4, 5:
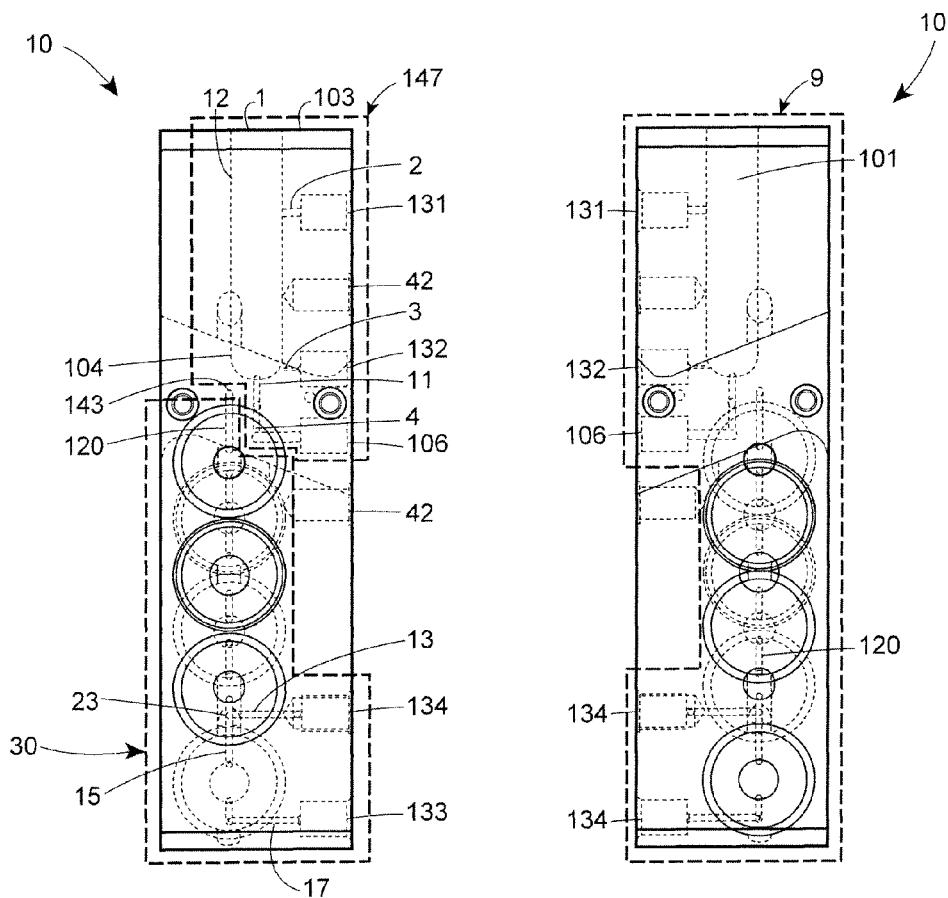
FIG. 4 illustrates a view of the integrated body along a line O-Y of FIG. 2B.
FIG. 5 illustrates a view of the integrated body along a line Y-O of FIG. 2B.
Figure 6:
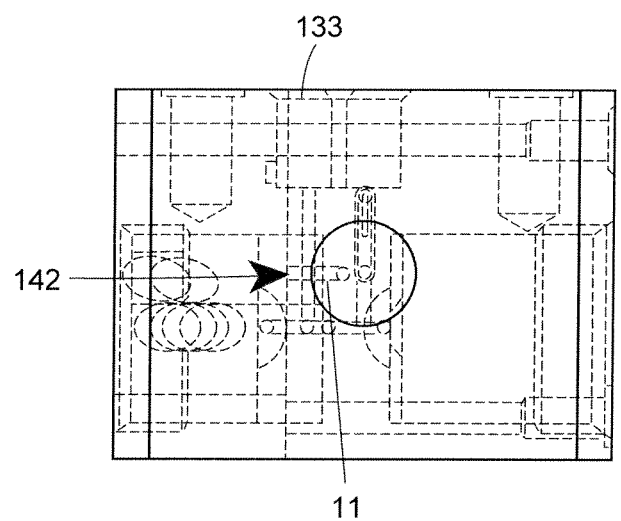
FIG. 6 illustrates a view of the integrated body along a line Z-O of FIG. 2B.

FIG. 5 indicates the features of integrated body 10 that make up flow path 9. FIG. 4 indicates the features of integrated body 10 associated with each of the two major sections of flow path 9. Flow path 9 includes upper path 47 proximate top surface 103 and flow cell 30 distal to top surface 103. Upper path 47 includes dilution cup 12, wash conduit 2, diluent conduit 3, drain conduit 4, transfer conduit 11 (best visible in FIG. 3), and isolation valve 24 (visible in FIG. 2A). Features of integrated body 10 that make up flow cell 30 are best visible in FIG. 3 and include main channel 21, electrodes docks 110-115, exit conduit 13, side channel 15, and reference conduit 17.

The primary purpose of upper path 47 is to accept a test solution and to prepare for measurement by mixing the test solution with diluent. Other purposes include draining fluids from integrated body 10 and, in some embodiments, rinsing probe 14 (shown in FIG. 1). Referring to FIGS. 3 and 4, upper path 47 includes four fluid conduits communicating with dilution cup 12: drain conduit 4, transfer conduit 11, diluent conduit 3, and wash conduit 2.

The central feature of upper path 47 is dilution cup 12, an elongated cavity oriented vertically (perpendicularly to top surface 103) in integrated body 10. The cavity is preferably of circular cross section for ease of fabrication and to reduce wash requirements by minimizing wetted surface area. The volume of dilution cup 12 may be in the range of 0.1 milliliters to 10 milliliters, preferably in the range of 0.5 milliliters to about 5 milliliters and most preferably about 1.8 milliliters. Opening 1 is disposed at top surface 103 of integrated body 10 and forms the upper boundary of dilution cup 12.

Bottom end 104 of dilution cup 12 tapers to drain conduit 4 to allow for near complete gravity draining. Preferably, bottom end 104 of dilution cup 12 is a hemisphere with connection to drain conduit 4 at the lowest point. The hemispherical shape reduces the likelihood of incomplete drainage by reducing fluid retention caused by surface tension at small radii. Drain conduit 4 leads to drain port 106 that may be used in conjunction with supporting fluidics 35 to drain dilution cup 12.

Diluent conduit 3 extends from diluent port 132 to dilution cup 12. The purpose of diluent conduit 3 is twofold: to add diluent to mix with test solution, and to aid in uniform mixing of resultant test solutions. Diluent port 132 supplies diluent from supporting fluidics 35 to one end of diluent conduit 3. The other end of diluent conduit 3 connects to dilution cup 12 at a position near bottom end 104. The location and configuration of the connection to dilution cup 12 is important for efficacy of mixing of diluent with test solution. Diluent conduit 3 may be directed tangentially to the circumference of dilution cup 12 to impart a swirling motion to contents during diluent injection. Alternatively, or additionally, diluent conduit 3 may be skewed at an angle to the horizontal (parallel to top surface 103) in order to impart a vertical component to the path of injected diluent. While either of these connection schemes may have value in assuring rapid and complete mixing of assay mixture, preferably, diluent conduit 3 is directed perpendicularly to the circumference of dilution cup 12 and toward the long axis of dilution cup 12. Preferably, diluent conduit 3 intersects dilution cup 12 within the hemispherical portion and parallel to top surface 103. This disposition, together with the injection sequence described in detail below, advantageously allows thorough mixing of test solution and diluent without any additional hardware other than probe 14. Among other factors, the short, straight path of diluent conduit 3 has low flow resistance, allowing external pressure to inject diluent with relatively high velocity.

Transfer conduit 11 allows fluid interchange between dilution cup 12 and flow cell 30. One end of transfer conduit 11 connects near bottom end 104 of dilution cup 12. The other end of transfer conduit 11 couples to first port 142 leading to isolation valve 24 (FIG. 2A). Fluid in dilution cup 12 below the level of connection of transfer conduit 11 is inaccessible for transfer to flow cell 30. Connection of transfer conduit 11 near bottom end 104 minimizes the amount of assay mixture required in dilution cup 12 by reducing the amount of inaccessible assay mixture. Transfer conduit 11 preferably connects to dilution cup 12 in the hemispherical region of dilution cup 12 in a direction roughly perpendicular to the hemispherical boundary to minimize hang up of fluid at the connection.

Wash conduit 2 allows wash fluid to enter and rinse dilution cup 12. Wash conduit 2 communicates with dilution cup 12 to deliver wash solution. While wash conduit 2 may intersect dilution cup 12 at any height, preferably wash conduit 2 intersects dilution cup 12 above the intersections of diluent conduit 3 and of transfer conduit 11, allowing rinsing of these intersections with clean wash solution. The end of wash conduit 2 distal to dilution cup 12 leads to wash port 131. Wash port 131 allows connection to supporting fluidics 35 as described above.

Isolation valve 24 selectively allows fluid transfer between first port 142 and second port 143 (collectively valve ports). As valve ports 142 and 143 are coupled via transfer conduit 11 to dilution cup 12 and to flow cell 30, isolation valve 24 controls fluid transfer between dilution cup 12 and flow cell 30. When isolation valve 24 is closed, no fluid may be transferred. When isolation valve 24 is open, fluid components may respond to differential pressure or diffusion by moving between dilution cup 12 and flow cell 30. Blocking flow between the two sections is advantageous because it assures that only thoroughly mixed and representative aliquots of assay mixture enter flow cell 30 for measurement of ion activities.

Flow cell 30 includes main channel 21 with coupled exit conduit 13, side channel 15, and reference conduit 17. Main channel 21 extends from second port 143 of isolation valve 24 to exit conduit 13 and to side channel 15. Side channel 15 branches from main channel 21 at intersection 23 and extends to reference conduit 17. Electrode docks 110-114 are disposed to contact fluids in main channel 21 at discrete locations along the extent of main channel 21. Reference electrode dock 115 is disposed to contact reference solution at the junction of side channel 15 and reference conduit 17. Preferably, main channel 21 is unbranched so that each element of fluid passing from isolation valve 24 to exit conduit 13 contacts each of ground electrode 6 and each analyte electrode 5 when the electrodes are mounted in electrode docks 110-114. This unbranched structure reduces unswept volumes that might otherwise cross-contaminate successive assay mixtures.

The purpose of main channel 21 is to transport fluids to and from the responsive areas of electrodes 5 and 6. Main channel 21 need not be straight; in some embodiments, such as that illustrated in FIGS. 2-6, main channel 21 may change directions by including channel segments 120 beginning at second port 143 of isolation valve 24 and disposed between each of electrodes 5 and 6. This direction change allows placement of electrodes 5 and 6 on alternate sides of integrated body 10. This alternate-side electrode placement allows more compact packaging of ISE system 40. In some embodiments, electrodes may be placed along a single side of integrated body 10 in a relatively spread out configuration, or along more than two sides producing a more compact assembly. Alternate-side electrode placement is preferred because it gives a reasonably compact assembly but preserves easy access for mounting and for electrode replacement.

In the embodiment of FIG. 2B, the six electrode docks 110-115 accommodate one ground electrode 6, four analyte electrodes 5, and one reference electrode 31. Each of electrode docks 110-114 may accommodate either one of analyte electrodes 5 or ground electrode 6. Electrode dock 115 accommodates reference electrode 31. Ground electrode 6 and analyte electrodes 5 may be intermixed in any order among electrode docks 110-114. While ground electrode 6 preferably occupies electrode dock 110 closest to isolation valve 24, the ability to place ground electrode 6 within any of electrode docks 110-114 allows optimization of positioning to control electrical noise.

In some embodiments, some of electrode docks 110-114 may be unoccupied. Integrated body 10 may be used with less than a complete complement of analyte electrodes 5 by providing an electrode plug (not shown) with shape comparable to the electrode it replaces.

In some embodiments, each electrode 5, 6, and 31 disposed in contact with flow cell 30 expose a generally planar responsive region to a generally cylindrical fluid channel. This mismatch in shape produces unswept dead volumes that require large volumes of fluids to prevent carryover. To prevent this, each of electrode docks 110-115 may include convex recess 48 aligned axially with each of electrode docks 110-115. Convex recess 48 overlies the responsive region of each of electrodes 5, 6, and 31 mounted in electrode docks 110-115. Channel segments 120 intersect each convex recess 48 to conduct fluid to and from electrodes 5 and 6. The combination of channel segments 120 and convex recesses 48 associated with electrode docks 110-114 constitutes main channel 21.

Each convex recess 48 is preferably a spherical cap to minimize surface area and to provide symmetrical flow independent of flow direction. The base diameter of each convex recess 48 is selected to be smaller than the internal diameter of face seal 8 and may encompass some or all of the active region 48 of each of electrodes 5, 6, and 31. Preferably, convex recess 48 has radius of about 0.125 inches with center displaced about 0.085 inches from the bottom of each electrode port 110-115 such that each convex recess 48 comprises less than a full hemisphere.

Main channel 21 continues beyond electrode port 114 to intersection 23. At intersection 23, the continuation of channel segment 120 originating at electrode port 114 becomes side channel 15. Exit conduit 13 connects to main channel 21 at intersection 23 and continues to exit port 134 where it connects to supporting fluidics 35 as discussed above. Side channel 15 extends to convex recess 48 associated with electrode dock 115. Reference conduit 17 extends from convex recess 48 associated with electrode dock 115 to reference port 133 where it connects to supporting fluidics 35 discussed above. Reference electrode 31 is disposed in electrode dock 115 and is exposed to reference solution transported through side channel 15 and reference conduit 17.

Each of reference solution and assay mixtures (the majority of which is diluent) are conductive fluids. When flow cell 30 is filled with reference fluid or a combination of reference fluid and assay mixture, electrodes 5, 6, and 31 are in electrical communication with one another. Analyte electrodes 5 and reference electrode 31 and external measurement electronics form an electric circuit for measuring an electric potential that is indicative of an ion activity of the fluids in flow cell 30. As discussed above, each analyte electrode 5 is an electrical half cell contributing to an electrode potential in response to target ion activity in the assay mixture. Reference electrode 31 acts as a second electrical half cell to support current flow producing measurable electrode potentials between reference electrode 31 and each analyte electrode 5. Ground electrode 6 electrically connects to system ground and, when in contact with assay mixture in main channel 21, grounds the otherwise floating contents of flow cell 30. Grounding assures compatibility of electrode potentials with measurement electronics, which normally have limited dynamic range centered at or near system ground and helps reject electrical noise from the electrode potentials.

Figure 7A:
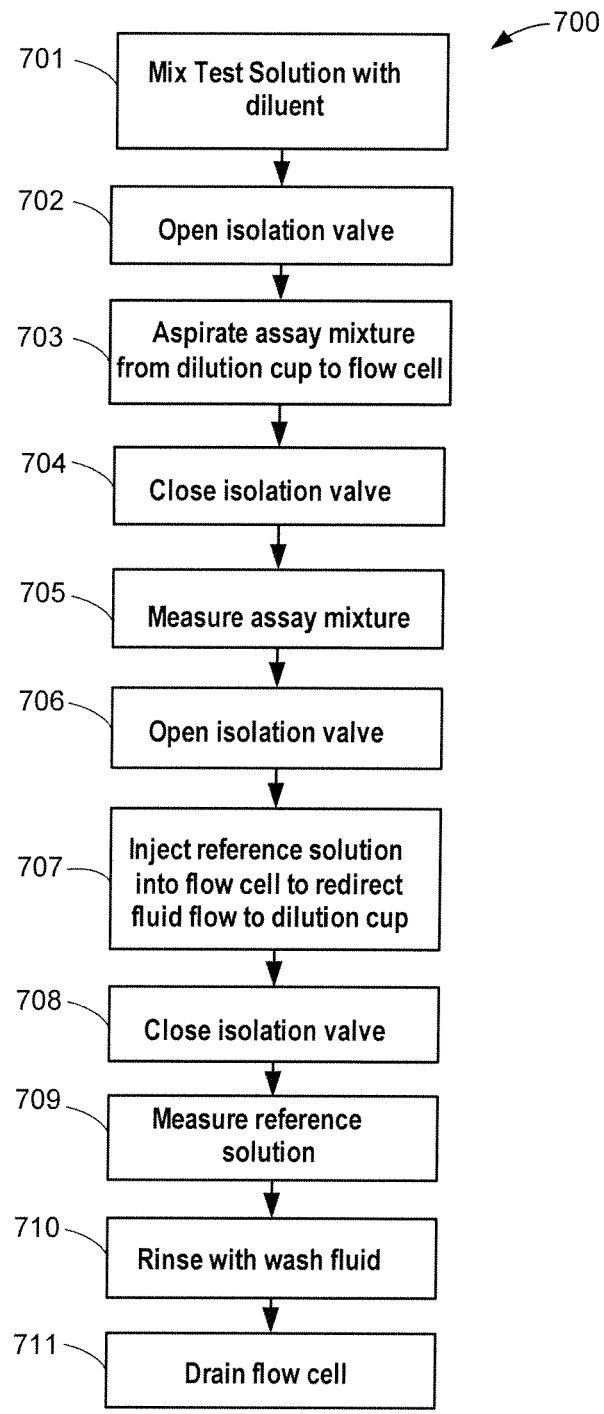
FIG. 7A illustrates a process of performing an ISE analysis using the described system.

Supporting fluidics 35 and external measurement electronics as discussed above cooperate with integrated assembly 50 to determine ion activities in test solutions. FIG. 7A illustrates process 700 of performing an ISE analysis using the described system. ISE analysis process 700 of FIG. 7A is best understood with reference to FIGS. 2A, 2B, 3, and 4 as they relate to flow path 9 and to FIG. 1 as it relates to supporting fluidics 35.

The ISE analysis includes two alternating measurement phases for each test solution. In the first measurement phase (shown in blocks 701 through 705), ISE system 40 prepares and measures potentials associated with the assay mixture. In the second measurement phase (blocks 706 through 709), ISE system 40 measures potentials associated with the reference solution. After the second measurement phase, ISE system 40 drains the used fluids and rinses dilution cup 12 so that ISE analysis process 700 may continue for a fresh test solution (blocks 710 and 711). ISE system 40 combines the results of the two measurement phases to determine the ionic activities of the test solution.

Since ISE analysis process 700 includes alternating measurement phases, flow cell 30 remains full of fluid at all times. If ISE analysis system 40 is left inactive for a prolonged period, it may be periodically flushed with reference solution to counter evaporation. Thus, at the start of each instance of ISE analysis process 700 flow cell 30 may be full of reference solution.

The first measurement phase includes blocks 701 through 705 and begins with a mixing process at block 701, described in more detail below in relation to FIG. 7B. The purpose of this process is to dilute the test solution with a known proportion of diluent to produce a uniformly mixed assay mixture.

After mixing, the assay mixture so formed may be transferred to flow cell 30 by first opening isolation valve 24 at block 702. With isolation valve 24 open, reference pump 34 may aspirate assay mixture from sample dilution cup 12 through transfer conduit 11 and isolation valve 24 to flow cell 30 at block 703. The volume aspirated is preferably sufficient to bring assay mixture beyond intersection 23 and slightly beyond port 134. The assay mixture remains substantially confined within integrated body 10 until exhausted as waste, reducing contamination of supporting fluidics 35.

Any liquid previously present in transfer conduit 11, isolation valve 24, and flow cell 30 is displaced into exit conduit 13 and towards bi-directional valve 37, reference valve 36, and reference pump 34. This displacement does not contaminate bi-directional valve 37, reference valve 36, and reference pump 34 as the liquid is the same reference solution normally wetting these components. As described above, side channel 15 remains filled with reference solution. The flow down main channel 21 "shears off" the reference solution in side channel 15 leaving it in contact with assay mixture from dilution cup 12. The juxtaposition of the two different fluids at intersection 23 of side channel 15 and main channel 21 forms a liquid junction. This liquid junction electrically couples reference electrode 31 (continuously exposed to reference fluid) and analyte electrodes 5 (exposed to assay mixture transferred from dilution cup 12).

Effective aspiration by reference pump 34 requires that bi-directional valve 37 be set to couple reference valve 36 to exit conduit 13. Reference valve 36 must be set to couple the outlet of reference pump 34 to bi-directional valve 37.

The first measurement phase continues with closure of isolation valve 24 at block 704 to isolate flow cell 30 from dilution cup 12. This advantageously reduces fluid motion at the responsive surfaces of electrodes 5, 6, and 31 that may produce electrical noise. Noise-inducing fluid motion may be associated with vibrations or with changes in atmospheric pressure such as that caused by opening or closing laboratory doors. Alternatively, isolation valve 24 may remain open.

Next, at block 705, external measurement electronics measure the potentials between analyte electrodes 5 and reference electrode 31 to determine ionic activities of the assay mixture. External measurement electronics suitable for use with ISE determinations are well known in the art and will not be described further.

The second measurement phase includes blocks 706 through 709 and begins with opening of isolation valve 24 at block 706. At block 707, reference pump 34 injects reference solution into flow path 9, forcing assay mixture in flow cell 30 back into sample dilution cup 12.

Reference solution may be added to flow cell 30 through either of two paths selectable by the setting of bi-directional valve 37. The use of two paths for reference solution injection allows both displacement of the assay mixture and renewal of the liquid junction at intersection 23. Injection through exit port 134 displaces assay mixture beyond intersection 23 back towards dilution cup 12. Injection through reference conduit 17 and side channel 15 advantageously counters any intermixing or diffusion of ionic species that may have occurred during the first measurement phase at the liquid junction at intersection 23. Once the assay mixture beyond intersection 23 has been cleared and the liquid junction has been renewed, either injection path may be used to displace the balance of the contents of flow cell 30 back into sample dilution cup 12.

Preferably, bi-directional valve 37 is first set to couple reference valve 36 to exit port 134 so that reference pump 34 may displace the assay mixture towards dilution cup 12. After the interface between reference solution and assay mixture has at least passed intersection 23, reference pump 34 may be temporarily halted and bi-directional valve 37 reset to couple reference valve 36 to reference conduit 17. Reference pump 34 then continues operation and pumps additional reference fluid through reference conduit 17, through convex recess 48 associated with electrode dock 115, through side channel 15 and main channel 21 toward injection cup 12. The assay mixture forced back into the sample dilution cup may be chased with an additional volume of reference solution to assure the second measurement phase samples only reference fluid.

Once the flow cell is flooded with the reference solution, isolation valve 24 may be closed (block 708) to isolate flow cell 30. External measurement electronics then measure the potentials between analyte electrodes 5 and reference electrode 31 to determine ionic activities of the reference solution, completing the second measurement phase at block 709.

ISE analysis process 700 continues after the second measurement phase with steps to prepare ISE system 40 for the next test solution. At block 710 dilution cup 12 may be flushed with wash fluid (e.g., de-ionized water) by injecting the wash fluid into port 131. At block 711, the contents of the sample dilution cup may be drained through port 106. Optionally, dilution cup 12 may be flushed in a two part operation; first the assay mixture and reference solution contents may be drained through port 106. Second, the sample dilution cup may be rinsed by wash fluid injected through port 131 and drained through port 106. The first part may occur earlier in process 700, partially overlapping the block 707 transfer of assay mixture from flow cell 30.

ISE analysis process 700 eventually drains the contents of reference pump 34 and diluent pump 20 in embodiments where these pumps are non-flow-through type pumps such as syringe pumps or piston pumps. Reference pump 34 and diluent pump 20 need to be refilled in such embodiments.

Reference pump 34 may be refilled with reference solution at any portion of ISE analysis process 700 when reference pump 34 is not otherwise engaged. Refill of reference pump 34 requires setting reference valve 36 to couple reference pump 34 to reference reservoir 32 and aspirating reference fluid into reference pump 34. In some embodiments, reference pump 34 may have sufficient capacity to service multiple cycles of ISE analysis process 700. Preferably, reference pump 34 is refilled in every cycle of ISE analysis process 700 to maintain conditions for each determination as constant as possible.

Similarly, diluent pump 20 may be refilled with diluent at any portion of ISE analysis process 700 when diluent pump 20 is not otherwise engaged. Refill of diluent pump 20 requires setting diluent valve 18 to couple diluent pump 20 to diluent reservoir 19 and aspirating diluent into diluent pump 20. In some embodiments, diluent pump 20 may have sufficient capacity to service multiple cycles of ISE analysis process 700. Preferably, diluent pump 20 is refilled in every cycle of ISE analysis process 700 to maintain conditions for each determination as constant as possible.

The purpose of the interleaved measurement of assay mixture and reference solution is to correct for any tendency of electrodes 5 and 31 to drift with time. Corrections for electrode drift based upon such interleaved measurements are well known in the art and will not be discussed further.

An additional benefit of the ISE analysis process 700 is that the addition of reference solution serves to displace the assay mixture from flow cell 30 with a minimum of external hardware; the same simple reference pump 34 alternately fills flow cell 30 with assay mixture and replaces it with reference solution. This advantageously reduces complexity and avoids many of the leakage and cross-contamination issues associated with prior art ratio pumps.

In some embodiments, reference pump 34 may comprise a pair of unidirectional pumps (not shown). Each unidirectional pump may be, for example, a peristaltic pump. The first unidirectional pump would be responsible for aspirating the contents of dilution cup 12 into flow cell 30. The second unidirectional pump would be responsible for injection of the reference solution and displacement of assay mixture back into dilution cup 12.

Figure 7B:
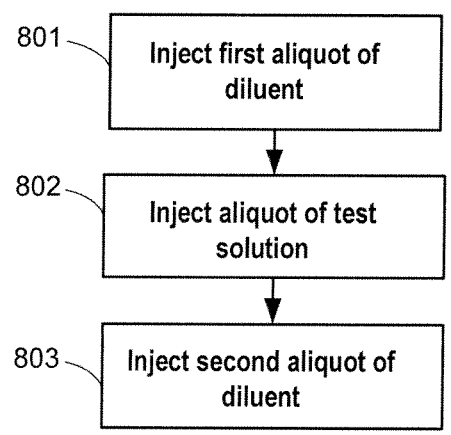
FIG. 7B illustrates a detailed mixing process using the described system.

FIG. 7B illustrates in further detail the mixing process of block 701. Mixing process 701 of FIG. 7B is best understood with reference to FIGS. 2A, 2B, 3, and 4 as they relate to flow path 9 and to FIG. 1 as it relates to supporting fluidics 35.

Probe 14 supplies test solution to dilution cup 12. Diluent pump 20 supplies diluent to dilution cup 12 through diluent valve 18, diluent port 132, and diluent conduit 3. Each step of the mixing process of block 701 is preferably performed with isolation valve 24 closed.

The mixing process of block 701 includes two diluent injections flanking a single test solution dispense. The sequence and character of the injections together with the geometrical features of integrated body 10 serve to assure effective mixing with minimal hardware complexity. Surprisingly, the relatively simple process produces mixing efficacy comparable to or superior to prior art solutions using active mixers such as stir bars and repeated cycles of "huff and puff" aspiration and dispensing. The mixing process of block 701 produced a two-fold improvement over prior closed injection port methods in coefficients of variation for sodium ion activity measurement, a test where precision is of paramount importance.

At block 801, diluent pump 20 injects a first diluent aliquot into dilution cup 12. The volume of the first diluent aliquot may be sufficient to submerge the junction of diluent conduit 3 and dilution cup 12.

At block 802, probe 14 descends into dilution cup 12 to a height slightly below the surface of the first diluent aliquot. Probe 14 then dispenses test solution such that the test solution droplet extruded from the tip of the probe 14 contacts the first diluent aliquot. The first diluent aliquot provides a fluid medium to receive the test solution, relieving the surface tension of the test solution causing the test solution to detach from probe 14 and merge with the first diluent aliquot. If no fluid medium were present, the surface tension of the test sample might cause the test sample to adhere to the tip of probe 14 or to the surface of dilution cup 12 and fail to adequately mix with the diluent.

The volumes of diluent and test solution in relation to dilution cup 12 are important determinants of mixing efficacy. Preferably, the test solution has volume of less than 40 microliters and most preferably of about 25 microliters in order to limit consumption of this hard-to-obtain material. The ratio of diluent to test solution in assay mixtures is chosen to optimize other performance variables and is generally in the range of about 10:1 to about 30:1 and preferably about 20:1. Preferably, the first diluent aliquot has volume approximately sufficient to fill the hemispherical lower portion of dilution cup 12 and most preferably about 100 microliters. The remaining volume of about 400 microliters needed to complete a 20:1 dilution ratio forms the second diluent aliquot.

In some embodiments, the test solution may be dispensed only after the first diluent aliquot is injected into dilution cup 12. Alternatively, in other embodiments, test solution may be dispensed substantially simultaneously with injection of the first diluent aliquot in such a manner as to cause the descending droplet of test solution to "kiss" the rising pool of the first diluent aliquot. In still other embodiments, where probe 14 characteristics allow and the test solution volume is sufficient to cause the test solution droplet to detach spontaneously from probe 14, probe 14 may dispense test solution from a height substantially above the fill level of the first diluent aliquot.

At block 803 diluent pump 20 injects a second diluent aliquot into dilution cup 12. The second diluent aliquot merges with and agitates the combination of the first diluent aliquot and the dispensed test solution. The merger and agitation provides a precise and thorough mixing of a particular volume of test solution with a particular volume of diluent. This completes the mixing process. In other embodiments, additional aliquots (e.g., a third or fourth aliquot) of diluent may be injected to further control the mixing of the test sample.

Without intent to be bound by theory, it is believed that the injection of the second diluent aliquot is particularly efficacious in completing mixing in part because it enters from beneath the surface of the liquid in dilution cup 12, roiling the volume without needing to break the tension of the liquid surface. Further, the proximity of the up-curving wall of the hemispherical portion of dilution cup 12 to the opening of diluent conduit 3 imparts an upward motion to the entering diluent, further agitating the mixture. Finally, the volume of the second diluent aliquot, more than twice that present in dilution cup 12 before injection of the second diluent aliquot, allows the dynamics of the entering diluent to dominate the behavior of the combined volume. The velocity of injection of the second diluent aliquot may be important in providing precise mixing with the test solution. An injection velocity of about 500 microliters per second has been found to produce adequate mixing.

Design Benefits

The design features and operation sequence of an indirect ISE interact to affect system performance, required test solution volume, size, and total cost. Improvements in one of these functional attributes usually involve degradation in others. The above described indirect ISE system escapes many of these tradeoffs; it allows improvement to more than one functional attribute without degradation in others.

One reason for the tight linkage of attributes is that a modern ISE system constantly interchanges the fluids that fill it, presenting to the electrodes in turn a first assay mixture, a reference solution, a second assay mixture, a reference solution, etc. Any amount of a previous fluid that remains within the system must be a small enough proportion of the next fluid that it contributes no more than a negligible effect on the measured result. Thus the volume of an ISE system has a two-fold influence on the amount of test solution required; first, enough assay mixture must be available to fill the volume; second, the volume of assay mixture must be much greater than any residual volume of a prior fluid. The amount of residual fluid depends upon the area of wetted surface and upon the geometry of that surface. Tight corners, complex shapes exposed to wetting, unswept dead volumes, and rough surfaces all increase the amount of residual fluid and require more assay mixture, and hence more of the scarce test solution.

Several elements of the invention contribute to reduced test solution requirements while enhancing other attributes. The integrated body eliminates the need for extra test solution required to fill connections between separate dilution cup and flow cell. It also reduces size, complexity, and cost by eliminating the extra part and the connection hardware. The ground electrode avoids the sharp corners and unswept volumes typical of earlier grounding plates, thereby reducing the amount of assay mixture required to rinse that area as well as the expense of installing the plate. The mixing design eliminates both the wetted surfaces of mechanical stir bars and their expense.

Several elements also contribute to enhanced system performance. The ground electrode may be installed similarly to the analyte electrodes by rotating its threaded body to compress a face seal. This improves performance over earlier glued-in ground connections by eliminating the contaminating effects of glue. The two-way flow process eliminates skewed potentials that may exist in multi-chamber ratio pumps by using a single reference pump to push and pull multiple fluids.

Thorough mixing is of particular importance to system performance in indirect ISE measurements as the material measured is not a pure substance but a mixture of test solution and diluent. The system exposes this assay mixture to several electrodes positioned at different points along a narrow channel. Each electrode reacts to a different local volume of assay mixture than does each other electrode. If the test solution is not consistently and uniformly mixed with diluent, then the local volumes may contain concentrations of analytes that are not representative of the bulk assay mixture. This degrades precision and risks result accuracy. The mixing features and method disclosed take advantage of divided fluid flows intelligently controlled to provide a uniform assay mixture. The local volume exposed to each electrode is consistent in test solution concentration with that at other electrodes and with that from other test solutions. This improves performance by reducing imprecision and increasing accuracy.

Several elements also contribute to reduce system size and total cost. The integrated body eliminates the need for a separate dilution cup and the interconnection hardware to plumb and mount it. The mix method replaces a stir bar, its drive circuitry, and their attendant maintenance with a "no cost" combination of cup geometry and process steps. The ground electrode eliminates the expense of grounding plate mounting and standardizes the ground electrode to the same form factor as the analyte electrodes, thus taking advantage of their higher production volume economy. The two-way flow process replaces a complex, fault-prone, multi-chamber ratio pump with a simple push-pull style pump. The pump contacts only reference solution even though it also controls the flow of the diluted assay mixture, thus avoiding the cross-contamination issues that plague earlier methods. The net result is a considerable saving in cost and space.

The disclosed embodiments may produce these improvements in system size and cost, in assay performance, and in the conservation of scarce test solution. While other concepts may be able to improve one or another of these attributes, this is usually at the cost of degradation in others. Improvements in each of the attributes contrary to expectations of tradeoffs among them, as achieved here, further illustrate the novelty and utility of the invention.

Although techniques and structures for determining electrolytes in a sample have been described above in terms of particular embodiments, it should be understood that the scope of the disclosure is defined by the words of the claims set forth at the end of this disclosure. The detailed description is to be construed as exemplary only and does not describe every possible embodiment because describing every possible alternative embodiment would be impractical, if not impossible. Numerous alternative embodiments could be implemented, using either current technology or technology developed after the filing date of this disclosure, which would still fall within the scope of the claims.

We claim:

1. A method of determining an electrolyte in a sample, the method comprising:
   adding the sample to an electrolyte module, the electrolyte module including a single, integrated body and a pump, the single, integrated body including a dilution cup and a flow cell, the dilution cup having a hemispherical bottom and being formed within the single, integrated body, the flow cell having a flow channel with a first end and a second end, the first end fluidically coupled to the dilution cup, and the second end fluidically coupled to the pump;
   combining the sample with a diluent in the dilution cup to produce a diluted sample;
   operating the pump to aspirate the diluted sample into the flow cell through the first end;
   measuring the electrolyte in the diluted sample in the flow cell; and
   reversing the pump to dispense a reference solution through the second end to displace the diluted sample from the flow cell back into the dilution cup and to fill the flow cell with the reference solution,
   wherein the flow cell further includes a side channel having a junction end and a free end, the junction end fluidically coupled to the flow channel at an intersection in between the first end and the second end,
   wherein a reference solution is added to the flow cell through either of two paths, wherein one of the two paths includes the side channel and the intersection, and wherein the other of the two paths includes the second end and the intersection; and
   wherein adding the reference solution to the flow cell through either of the two paths includes actuating a bidirectional valve to direct the reference solution through one or the other of the two paths.

2. The method of claim 1 further comprising draining the displaced diluted sample from the dilution cup.

3. The method of claim 1 wherein operating the pump includes removing flow channel contents through the second end, thereby forming a liquid junction at the intersection.

4. The method of claim 1 further comprising configuring an isolation valve on the electrolyte module between the dilution cup and the flow cell, and wherein operating the pump includes opening the isolation valve.

5. The method of claim 4 wherein measuring the electrolyte includes closing the isolation valve.

6. The method of claim 1 wherein combining the sample with a diluent includes injecting a first diluent aliquot, adding the sample, and injecting a second diluent aliquot.

7. The method of claim 6 wherein the volume of the second diluent aliquot is greater than the sum of the volumes of the first diluent aliquot and the sample.

8. The method of claim 7 wherein the injection rate of the second diluent aliquot is about 500 microliters per second.

9. The method of claim 8 further comprising rinsing the dilution cup.

10. A method of determining an electrolyte in a sample, the method comprising:
    providing an electrolyte module including a single, integrated body having a dilution cup and a flow cell, the dilution cup and the flow cell formed within the integrated body, the dilution cup having an open top, a hemispherical bottom, and a diluent conduit fluidically connected to the dilution cup, the flow cell disposed between the dilution cup and a reference pump, wherein the reference pump is configured to dispense reference solution by delivering the reference solution from a reference container to the flow cell through an end of the flow cell opposite the dilution cup;

forming a diluted sample in the dilution cup by injecting a first diluent aliquot, adding the sample, and injecting a second diluent aliquot; and measuring the electrolyte in the diluted sample, wherein the volume of the second diluent aliquot is greater than the sum of the volumes of the first diluent aliquot and the sample.

11. The method of claim 10 further comprising connecting the diluent conduit to the dilution cup within the hemispherical bottom so that the diluent conduit extends parallel to the open top, and injecting the second diluent aliquot into the dilution cup through the diluent conduit.

12. The method of claim 11 wherein the injection rate of the second diluent aliquot is about 500 microliters per second.

13. The method of claim 10 wherein the electrolyte module further includes a transfer probe movably disposed with respect to the dilution cup and aligned with the open top, and wherein the sample enters the dilution cup through the transfer probe.

14. The method of claim 1, wherein the dilution cup has an open top.

15. The method of claim 1, further comprising: cleaning a probe in the dilution cup.

16. The method of claim 1, wherein cleaning the probe comprises:

substantially filling the dilution cup with clean wash fluid;

inserting the probe into the clean wash fluid in the dilution cup to rinse the outside of the probe;

removing the probe from the wash fluid; and flushing the wash fluid from the dilution cup.

\* \* \* \* \*